(12) United States Patent
Feliss et al.

(10) Patent No.: US 7,278,967 B2
(45) Date of Patent: Oct. 9, 2007

(54) HARD DISK DRIVE MEDICAL MONITOR WITH MIRRORED HDDS

(75) Inventors: Norbert Feliss, Sunnyvale, CA (US); Donald Ray Gillis, San Jose, CA (US); Karl Arthur Flechsig, Los Gatos, CA (US)

(73) Assignee: Hitachi Global Storage Technologies Netherlands, B.V., Amsterdam (NL)

( * ) Notice: Subject to any disclaimer, the term of this patent is extended or adjusted under 35 U.S.C. 154(b) by 174 days.

(21) Appl. No.: 10/881,990

(22) Filed: Jun. 29, 2004

(65) Prior Publication Data

US 2005/0288562 A1 Dec. 29, 2005

(51) Int. Cl.
*A61B 5/00* (2006.01)

(52) U.S. Cl. ............... 600/300; 128/899; 128/903; 128/904; 128/905

(58) Field of Classification Search ........ 600/300–301; 128/899, 903–905, 920–925; 361/685; 607/30–32; 248/694; 711/114
See application file for complete search history.

(56) References Cited

U.S. PATENT DOCUMENTS

| 5,511,553 | A | | 4/1996 | Segalowitz | 128/696 |
|---|---|---|---|---|---|
| 5,628,310 | A | | 5/1997 | Rao et al. | 128/633 |
| 6,005,768 | A | * | 12/1999 | Jo | 361/685 |
| 6,083,248 | A | * | 7/2000 | Thompson | 607/30 |
| 6,175,752 | B1 | | 1/2001 | Say et al. | 600/345 |
| 6,201,980 | B1 | | 3/2001 | Darrow et al. | 600/347 |
| 6,283,438 | B1 | * | 9/2001 | Shimada et al. | 248/694 |
| 6,354,299 | B1 | * | 3/2002 | Fischell et al. | 128/899 |
| 6,402,689 | B1 | | 6/2002 | Scarantino et al. | 600/300 |
| 6,438,407 | B1 | | 8/2002 | Ousdigian et al. | 600/510 |
| 6,497,655 | B1 | | 12/2002 | Linberg et al. | |
| 6,609,023 | B1 | | 8/2003 | Fischell et al. | 600/515 |
| 6,641,533 | B2 | | 11/2003 | Causey, III et al. | 600/300 |
| 2002/0028991 | A1 | | 3/2002 | Thompson | 600/372 |
| 2002/0052539 | A1 | | 5/2002 | Haller et al. | 600/300 |
| 2002/0107557 | A1 | | 8/2002 | Edell et al. | 607/60 |
| 2002/0123673 | A1 | | 9/2002 | Webb | |
| 2003/0004403 | A1 | | 1/2003 | Drinan et al. | 600/301 |
| 2003/0028725 | A1 | * | 2/2003 | Naberhuis et al. | 711/114 |
| 2004/0088027 | A1 | | 5/2004 | Burns | |
| 2004/0181262 | A1 | | 9/2004 | Bauhahn | |
| 2004/0199212 | A1 | * | 10/2004 | Fischell et al. | 607/32 |

\* cited by examiner

*Primary Examiner*—Max Hindenburg
*Assistant Examiner*—Filip A. Kowalewski
(74) *Attorney, Agent, or Firm*—Larry B. Guernsey; Intellectual Property Law Offices

(57) ABSTRACT

A medical monitor is disclosed for implantation in a human body for monitoring biological activity and states as detected by implanted sensors. The medical monitor includes a primary disk drive and a secondary disk drive, where the secondary disk drive mirrors the primary disk drive. An enclosure surrounds at least one of the primary and secondary drives. A transmitter and receiver for produces and transmits signals. The medical monitor is in communication with the sensors, by which information on biological activity and states is stored on the primary disk drive, and the secondary disk drive.

8 Claims, 6 Drawing Sheets

HARD DISK DRIVE MEDICAL MONITOR WITH MIRRORED HDDS

The present application is related to patent applications entitled Rechargeable Hard Disk Drive Medical Monitor, U.S. application Ser. No. 10/881,989, Hard Disk Drive Medical Monitor With Security Encryption, U.S. application Ser. No. 10/881,952, Hard Disk Drive Medical Monitor With Sound-Proofing, U.S. application Ser. No. 10/881,040, Hard Disk Drive Medical Monitor With GPS, U.S. application Ser. No. 10/881,418, Hard Disk Drive Medical Monitor With Sound-Proofing, U.S. application Ser. No. 10/880,627, Hard Disk Drive Medical Monitor With Electrical Grounding System, U.S. application Ser. No. 10/881,419, and Hard Disk Drive Medical Monitor With Alert Signaling System, U.S. application Ser. No. 10/882,012, which are commonly assigned and filed contemporaneously.

BACKGROUND OF THE INVENTION

1. Field of the Invention

The present invention relates generally to methods and devices for monitoring of biological activity, and more particularly to a medical hard disk drive monitor to be implanted in a patient for gathering and monitoring of the patient's medical information.

2. Description of the Prior Art

Advances in medical science are now making possible treatments for many diseases and disabilities which would have been impossible before. Accurate diagnosis is crucial for treatment in most medical situations, and accumulation of data is nearly always a pre-requisite to accurate diagnosis. Certain medical conditions require accumulation of data over a long period of time in order to identify patterns in symptoms or trends in biological parameters which may be monitored, such as heart rate, blood pressure, enzyme levels in the blood stream, etc. This accumulated data over the course of many days, weeks, or even years must be collected and organized for analysis. With the continuing miniaturization of data storage devices, such as hard disk drives (HDDs), it has become possible to implant data storage devices into a patient's body, so that data from implanted sensors can be more easily collected. The ever-expanding capacity of these data storage devices means that data can be gathered for longer and longer periods without removal or replacement of the HDD.

Prior medical HDD monitors have been found to have certain limitations and to lack certain desirable features. In particular, it would be desirable that since the device is implanted in the user's body that it be provided with a power source which is easily recharged without subjecting the user to unnecessary surgery. It is also desirable that the data collected and transmitted by the medical HDD monitor would be encrypted, to ensure the user's privacy. Another desirable feature is that the HDD monitor would have an included mirrored HDD to make sure that the data, which may literally be a matter of life and death to the user, is held in a back-up copy. An additional desirable feature is that the medical HDD monitor would be sound-proofed, to provide the user with privacy, and to avoid occasional embarrassment. It is also desirable that the medical HDD would be provided with a system for tracking the user's whereabouts, in case of a medical emergency. Another desirable feature would be that the medical HDD be prevented from shocks and concussions by a shock protection system. A further desirable feature would be for the medical HDD monitor to be provided with an electrical grounding system to protect the medical HDD monitor, so that in case of exposure to high voltage or current spikes, perhaps while the user is being resuscitated by a defibrillation device, the medical HDD is not damaged. Also, it would be desirable that the medical HDD monitor be equipped with a signaling device that could alert either the user or medical personnel in case of a detected medical emergency or condition.

Thus there is a need for a medical HDD monitor which would be protected from intrusion by encryption of information, would also be available in a redundant mode, would have transmission signals in the radio frequency range, would be fabricated with sound-proofing materials, would be equipped to communicate with satellite communication signals via the public GPS frequencies and protocol, would also be available with materials and electronics that adequately ground the drive from exposure to high voltage or current spikes, would be easily rechargeable with minimal disturbance to the user, and which is also protected from mechanical shocks and concussions.

SUMMARY OF THE INVENTION

A medical HDD monitor, comprised of one or more hard disk drives for data redundancy, is used for data information gathering and data storage from one or more transducers which are implanted in the physical body of the user who is being monitored. The hard disk drive medical monitor is housed in a series of units for shock-proofing and sound-proofing. Data communication between the hard disk drive and the user or medical personnel is accomplished by RF signals which are encrypted for security reasons. Additional electronics are available for communication with a satellite which can transmit emergency signals to medical personnel that will relay information for ambulance pickup or other medical purposes. A signaling system provides an alert to the user or to medical personnel in case of an emergency or if certain medical states or conditions are detected.

The medical HDD monitor is protected against corrosion and oxidation behavior of the body plasma and other chemicals or by-products of the human body. An inert material surrounding the device protects the hard drive and its components from the corrosive and oxidative nature of the human body. An electrical grounding system is provided which can protect the medical HDD monitor from high voltage and current spikes. A recharging system allows rechargeable batteries to be charged without removing the medical HDD monitor or its batteries from the user's body.

Accordingly, it is an aspect of the present invention to present a medical HDD monitor that is protected from intrusion by encryption of information. All data stored in the hard drive is encrypted and access is only available to users with a proper ID and password. This ensures safeguarding any medical information from intruders.

Another aspect of the invention is to present a medical HDD monitor which is available in a redundant mode so there are optionally 2 hard drives, one for storage of the data and the other for a mirror backup. The data is constantly backed up whenever new data enters the drive. In the event one drive should be damaged or quit working, the second or backup drive is available for gathering information and transmitting this information to the owner.

And another aspect of the invention is to present a medical HDD monitor which produces transmission signals in the radio frequency range. These can either be public or private. Each transmission signal is customizable for specific applications.

A further aspect of the present invention is to present a medical HDD monitor which is fabricated with sound-proofing materials which allows ultra-quiet running and performance. The noise threshold of the drive is selectable by the user so shock proofing materials can be manufactured on the top, bottom and sides of the hard drive.

An additional aspect of the present invention is to present a medical HDD monitor which is equipped to communicate with satellite communication signals via the public GPS frequencies and protocol. The hard drive is also equipped with an electronic emergency signal so that when a medical emergency should arise, i.e. heart attack, heart fibrillation, high blood sugar, etc. a signal goes out on the GPS frequencies to advance warning selectable Doctors or Emergency crews who could relay the information to an ambulance.

Yet another aspect of the present invention is to present a medical HDD monitor which includes materials which help in preventing the drive from exposures to high shock and vibration situations. If the user were to be in a high g-force environment, i.e. flying an experimental plane, the materials surrounding the drive would protect it from the high g-forces and prevent a head crash or hard errors.

A yet further aspect of the present invention is to present a medical HDD monitor which is available with materials and electronics that adequately ground the drive from exposure to high voltage or current spikes. If the user were to be resuscitated by a defibrillation device, the hard drive is protected from the high voltage and current spikes applied to the chest cavity. These voltage and current spikes are not transmitted to the hard drive but are either buffered or grounded from entering the environment of the hard drive.

An additional aspect of the present invention is to present a medical HDD monitor which is protected against corrosion and oxidation behavior of the body plasma and other chemicals or by-products of the human body. Exposure to fluids in the human body would lead to corrosion and oxidation of electronic components which would lead to failure of the hard drive. An inert material surrounding the drive has the ability to protect the hard drive and its electronics from the corrosive and oxidative nature of the human body.

Briefly, one embodiment of the present invention is a medical monitor for implantation in a human body for monitoring biological activity and states as detected by implanted sensors. The medical monitor includes an enclosure surrounding at least one hard disk drive, and also includes a transmitter and a receiver for producing and transmitting signals in the radio frequency range. The medical monitor is in communication with the sensors, by which information on biological activity and states is stored on the one or more hard disk drives. It also includes a recharging system including at least one rechargeable battery and an induction electronics interface. The battery state is logged continuously on the hard disk drive. If the voltage level changes with time are not within the specifications given by the manufacturer then an algorithm that computes the slope of the discharge or current drain rate with time can predict how long the battery pack can survive without recharging.

An advantage of the present invention is that batteries can be recharged without removing the batteries or the medical monitor from the user's body.

Another advantage of the present invention is that it includes an alert mechanism, which can be of many different types to alert the user or medical personnel of medical conditions or of necessary battery recharge.

And another advantage of the present invention is that the medical monitor system includes a grounding device which can protect the medical monitor from high voltage or current spikes, in case defibrillation equipment is used to revive the user.

A further advantage of the present invention is that the medical monitor can be programmed and communicated with through radio frequency communications by an external programming device, and that these communications are preferably encrypted to ensure privacy.

A yet further advantage is that the medical monitor is protected by shock-proofing material which preferably includes one or more miniature air bags to prevent damage to the disk drive or drives.

These and other features and advantages of the present invention will no doubt become apparent to those skilled in the art upon reading the following detailed description which makes reference to the several figures of the drawing.

IN THE DRAWINGS

The following drawings are not made to scale as an actual device, and are. provided for illustration of the invention described herein.

DETAILED DESCRIPTION OF THE PREFERRED EMBODIMENTS

Figures 1A, 1B:
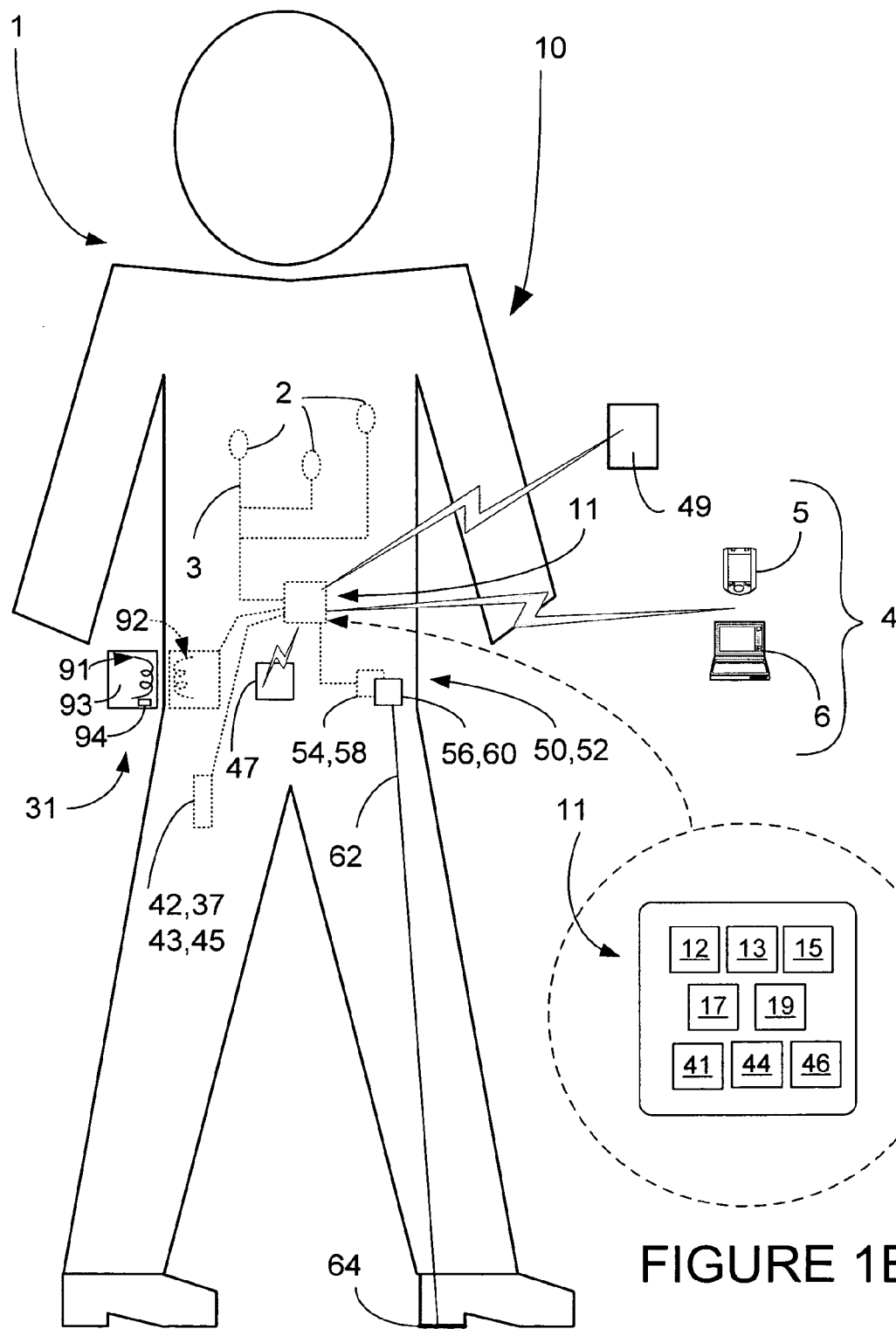
FIG. 1A is a schematic diagram of the medical HDD monitor of the present invention and associated components located in and around a user's body.
FIG. 1B is a detail view of the medical HDD monitor of the present invention

An embodiment of the present invention is a medical hard disk drive device and system. As illustrated in the various drawings herein, and particularly in the view of FIG. 1, a form of this preferred embodiment of the system of the inventive device is depicted by the general reference character 10 and for ease of reference, the medical hard disk monitor device will be referred to as medical HDD monitor 11.

Generally, the presently preferred embodiment of medical HDD monitor 11 includes one or more hard disk drives that are encapsulated into a square box approximately one inch thick with a length and width around three inches square. It is placed surgically in the lower abdomen, just underneath the skin (subdermal implantation), on the right or left side of the body. It can also be surgically implanted into the chest cavity for proximity to the heart and lungs in a data monitoring arrangement for closely following these vital organs. The medical HDD monitor 11 is implanted under the skin via local or general anesthesia. The medical HDD monitor 11 is battery operated and longevity of the battery preferably ranges at least five years. When the battery level is low, even after attempts at recharging, an alarm will sound indicating it needs to be replaced surgically. The alarm system will also indicate when the body transducers indicate either an abnormally high or low level. The medical HDD monitor 11 will also contact the doctor or nurse team when these alarms occur. The programmer in the doctor's office, or at the hospital, will tell via computer what the alarm is for and how to process the fault indication.

FIG. 1A shows a patient 1 which has been fitted with a number of monitor sensors 2. These sensors 2 are one or more transducers which collect data on the state of various bodily functions of the patient such as heart rate, blood pressure, blood sugar levels, etc. and report them to the medical HDD monitor 11, also shown in a detail view in FIG. 1B. The medical HDD monitor 11 has preferably been surgically implanted in the patient's body, preferably in the abdomen or chest area. The sensors 2 communicate with the medical HDD monitor 11 by radio frequency transmissions, or by micro-cables 3 which connect to the medical HDD monitor 11, where data is stored for later retrieval and analysis. The medical HDD monitor 11 may be set to take samples from the sensors 2 at regularly scheduled intervals, or the data collection may be triggered by some events, such as a detected irregularity of heartbeat, change in blood pressure, etc.

The user 1, programmer, doctor, nurse or medical team preferably uses an external programming device 4, to program the initialization and then the final setup of the medical HDD monitor 11. The external programming device 4 is preferably a small computer, handheld (PDA) 5 or laptop model 6, which allows data transfer to and from the medical HDD monitor 11 via a wire-less transceiver personal network.

FIG. 1B shows a detail view of the medical HDD monitor 11, which includes at least one hard disk drive (HDD) 12, as well as a radio frequency receiver 13 and transmitter 15. As discussed below, the medical HDD monitor 11 transmitter and receiver include a GPS receiver 46 and GPS transmitter 41 to communicate with satellite communication signals via the public GPS frequencies and protocol. The medical HDD monitor 11 is also preferably equipped with encryption software 44 which is set up with a user ID and password system 19, and a log of intrusions 17, or attempted intrusions, which can be accessed by the user 1 or by authorized medical personnel through the external programming device 4, as necessary.

Figure 2:
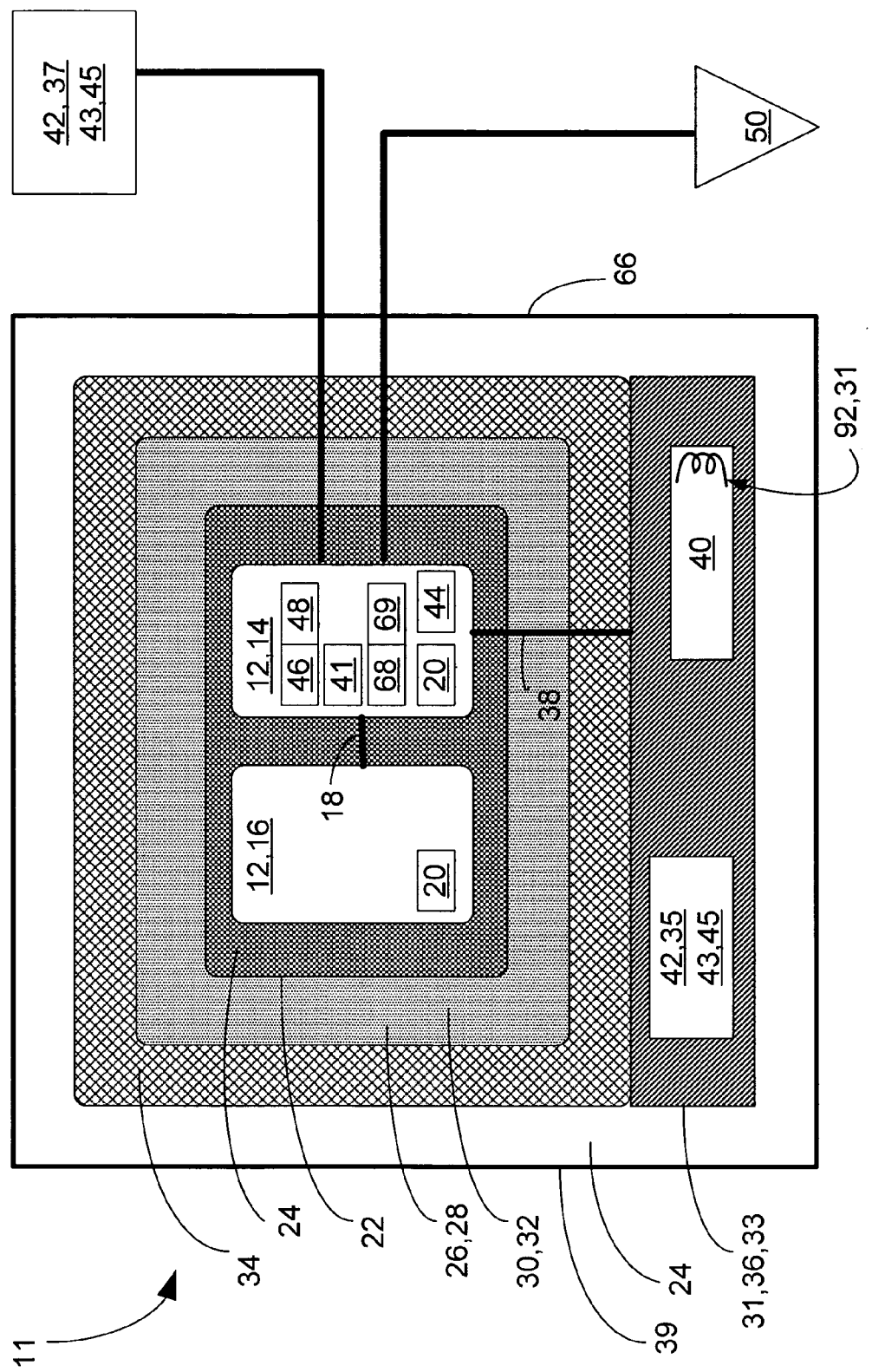
FIG. 2 shows a block diagram of a first embodiment of the medical HDD monitor of the present invention, which uses a twin HDD system.

FIG. 2 shows a detail view of one preferred embodiment of the medical HDD monitor 11. The medical HDD monitor 11 includes 2 hard disk drives 12 which are mounted near each other for digital data redundancy. Preferably, there is a primary hard disk drive 14 for gathering the biological information from the sensors (see FIG. 1) in the patient's body and a secondary hard disk drive, 16 which provides digital redundancy and data backup for the primary hard disk drive 14. An I/O connection, 18, is used to provide communication between the primary and secondary drives 14, 16. Typically, the secondary hard disk drive 16 would be supported as a "mirror" or "stripping" or combination of both "mirroring" and "stripping" drive to the primary hard disk drive 14 providing redundant backup data storage. There are 3 techniques to implement the disk drive data redundancy and data storage backup via RAID 0, RAID 1 and RAID 0+1 configuration. Only one configuration out of the 3 described can be used for the medical monitor's disk drives. The user or medical team can decide which is the best configuration to be used based on the best backup performance and fault tolerance acceptable and desired. This is usually decided on a case-by-case basis before the medical monitor is implanted into the patient.

RAID 0 is called data stripping and optimizes two identical hard disk drives to read and write data in parallel, interleaved stacks. Two hard disk drives perform the same work as a single disk drive but at a sustained data transfer rate, double that of a single disk alone, thus improving data access and storage. RAID 1 is called data mirroring that allows the device to copy and maintain an identical image of data from one drie to a second drive. If one drive fails, the disk array management software directs all applications to the surviving drive as it contains a complete copy of the data in the other drive. This RAID configuration provides data protection and increases fault tolerance to the entire system. RAID 0+1 is data stripping and data mirroring combined without parity (redundancy data) having to be calculated and written. The advantage of RAID 0+1 is fast data access (like RAID 0), but with the ability to lose one drive and have a complete duplicate surviving drive or set of drives (like RAID 1). The backup configuration software 20 to provide disk mirroring is written into the operating system of both drives. A battery pack 36 is used to provide power for the hard disk drives 14, 16.

It is of course desirable that the overall package, and thus the included disk drives 14, 16 be as small as possible, to be minimally intrusive to the patient. Presently, Hitachi Microdrives are favored for use, as they can each hold 4 GB of data, and are each roughly 1¾"×1½", although it is to be understood that any very small size hard disk drive can be used, and the invention is not intended to be limited to any particular make or model of disk drive or storage device. They are also not limited by small size since larger 2.5" drives can also be used for this purpose.

The inner enclosure 22 of the medical HDD monitor 11 is fabricated with a sealant 24 of inert materials that make it impervious to the leakage of body fluids. Materials used for this sealant could include inert epoxy sealants.

Besides sealants, additional materials are used to prevent the drive from exposures to high shock and vibration situations. For high g-force environments, materials are chosen that surround the cavity of the hard disk drive package to protect the system from high shock and prevent hard disk drive catastrophic crash or the generation of hard errors. A shock-proofing system 26 is used which includes one or more miniature polyethylene air bags 28 which surrounds the inner enclosure 22 of the medical HDD monitor 11. Preferably the shock-proofing system 26 includes an upper bag 30 and a lower bag 32.

The medical HDD monitor 11 is also preferably fabricated with sound-proofing materials, 34 which will allow ultra-quiet and ultra-low vibration during running. There are several materials which are presently preferred for sound-proofing. These include acoustic film or foam made of polyurethane. These can be also modified with barriers made of vinyl. Melamine Sheet Foam which is a product made from melamine resins is also a possible material, and has the advantages that it is fire, temperature and chemical resistant and halide free. Film faced acoustic film made of PVC sprayed onto glass cloths, neoprene coated glass cloth, and polyurethane coated glass cloth can also be used. These coated cloths are then laminated with any of the following products: polyurethane film, perforated or full formed PVC, reinforced Aluminum foil, metalized polyester film and black viscose tissue.

A battery pack 36 is used to provide power for the hard disk drives 14, 16. The power is supplied to the disk drive 14 via a series of wires 38. Induction electronics and interface 40 are provided to allow re-charging of the battery pack 36 from external electrical induction equipment, which will be discussed in more depth below.

An outer enclosure 39 is also of material which is highly resistant to corrosion and may include sealant 24 such as that discussed above in relation to the inner enclosure 22. The outer enclosure 39 is preferably a square box approximately one inch thick with a length and width around three inches square.

The medical HDD monitor 11 is preferably protected from data intrusion via encryption of all data storage information. All digital data stored in the hard drive is encrypted by public domain. type software encryption 44. The information is available only to the user and/or Doctor/Medical staff support team with a proper ID and password. Any intrusion by non-users would be safeguarded by encryption of all medical information, and a log of unlawful intrusive data entries would be kept by the medical HDD monitor 11 in a stored file.

The medical HDD monitor 11 communicates in the radio frequency range which is endorsed by the FCC. The transmission signals can be customizable for a broad range of frequencies depending on the type of transmission and receiving equipment available. The transmission frequencies are to be either public or private. Some medical HDD monitor 11 can be selectable in the types of broadband communication commonly used, i.e. "blue-tooth" technology, GSM band technology, etc.

The medical HDD monitor 11 is also preferably equipped with GPS technology module including a GPS receiver 46 and RF transmitter 41 to communicate with satellite communication signals via the public GPS frequencies and protocol. The RF transmitter covers transmission to a local cell phone network, Global Star Satellite, WiFi network, government licensed or unregulated telemetry receiver.

The basic principle inherent in GPS is to determine with the best possible accuracy a point in space, as defined by 3 coordinates, here geographical latitude and longitude as well as elevation above sea level. This is done by means of triangulation and involves the determining of distances to at least 3 GPS satellites from the user's GPS receiver which is embedded in the medical HDD monitor 11. The positions of the 3 satellites in space are known at all times by various observations methods and orbital computational methods. When one distance is known, the user must be located on the surface of a sphere with the satellite at the center with a radius equal to this distance. With 2 distances known, 2 points are possible of which one will be far out in space and can be eliminated. Thus, the point in space can be determined by calculation.

The distance of the satellite is determined by measuring the arrival time of the signal from the GPS satellite. This signal carries timing information from the atomic clock on-board the satellite and the measure time delay indicates the distance (multiply the time delay by the speed of light which gives the distance). The GPS receiver has a internal clock but the precision of this clock is much less than that of the atomic clocks in the satellites. The receiver clock will be some fractions of a second off but the time can still be measured. The precise time measurement makes use of the fact that the time offset of the clock in the GPS receiver 46 in the medical HDD monitor 11 is considered as the fourth unknown (the first 3 are the space coordinates of the receiver). In the first approximation, the offset is considered to be zero. If a fourth satellite signal is received and a fourth distance is measured it will also be possible to determine with high precision this time offset and then to find the correct space coordinates.

The 4 distances to the 4 satellites will only fit and determine one particular point in space, if the time offset has a certain value. This calculation is done automatically by the software in the GPS receiver 46 embedded in the medical HDD monitor 11. Thus, at least 4 satellites are needed for a satisfactory measurement. There are at least 24 operational GPS satellites at all times operated by the U.S. Air Force, each with an orbital period of 12 hours. The location of all the satellites is included in the satellite transmissions and this is stored in the hard drive of the GPS monitor. By calculating how far a satellite is via a software algorithm, the GPS receiver 46 in the medical HDD monitor 11 can know where it is located somewhere on the surface of an imaginary sphere centered at the satellite. It then determines the sizes of several spheres, one for each satellite. The medical HDD monitor 11 is located where these spheres intersect, and thus the location of the user, with the medical HDD monitor 11, can be tracked at all times.

The digital signals from the GPS satellites preferably are emitted at 2 frequencies: 1228 and 1575 Mhz. They are received by the GPS receiver 46 in the medical HDD monitor 11 and contain much detailed information. In addition to the timing signal, there are also data for the identification of the satellite (its number), about the status of the satellite clock, the satellite orbit, the current status of the satellite (health) and various correction data. The data is divided into frame of 1500 bits; one frame is transmitted in about 30 seconds. These data are stored in the medical HDD monitor 11 and updated regularly. The approximate directions and distances to individual GPS satellites that are momentarily above the horizon are calculated from the orbital data. In practice, due to the uncertainties in all the GPS measurements, i.e. errors due to reflections off surrounding elements, trees, houses, etc. the resolution of the GPS embedded instrument in the medical HDD monitor 11 is good to about +/−15 meters.

Now also referring to FIG. 1, the medical HDD monitor 11 is to be manufactured with materials and electronics that adequately ground the system from exposure to high voltage and current spikes. If a user were to be resuscitated by a defibrillation device, the medical HDD monitor 11 would be protected from the high current spikes applied to the chest cavity. These voltage and current spikes would not be transmitted to the medical HDD monitor 11. The materials used surrounding the medical HDD monitor 11 would transmit or ground the voltage or current spikes and direct them away from the electronics to a grounding structure 50.

The grounding structure 50 of the medical HDD monitor 11 preferably is a grounding receptacle 52 that includes an implanted receptacle 54 and optionally a mating non-implanted receptacle 56 (see FIG. 1). The implanted grounding receptacle 54 is preferably a metalized plate 58 which is made of conductive metal, i.e. stainless steel, or aluminum and which directs the high voltage spikes or current spikes away from the medical HDD monitor 11. The charge from this plate 58 is slowly dissipated throughout the human body since the grounding plate 58 is already immersed in a conductive bodily fluid. A charge on the grounding plate 58 will be conducted away by the electrical action of the body's muscle and fiber cells.

One type of non-implanted grounding receptacle 56 may be an external plate 60 to be carried by the user adjacent to the internal plate 58. If the high voltage spike is large enough potential, it will direct the voltage from the implanted metalized plate 58 across the skin interface and directly onto the external plate 60 that is carried by the user, i.e. on a belt, etc.

The non-implanted grounding receptacle 56 carried on the user's belt can also be wired to an external grounding wire 62 that is carried by one or both shoes 64. This allows a high voltage spike to be transferred from the inside of the body, to the non-implanted grounding receptacle 56 on the belt, to the shoes 64 and then to the earth via the shoes 64.

Figure 3:
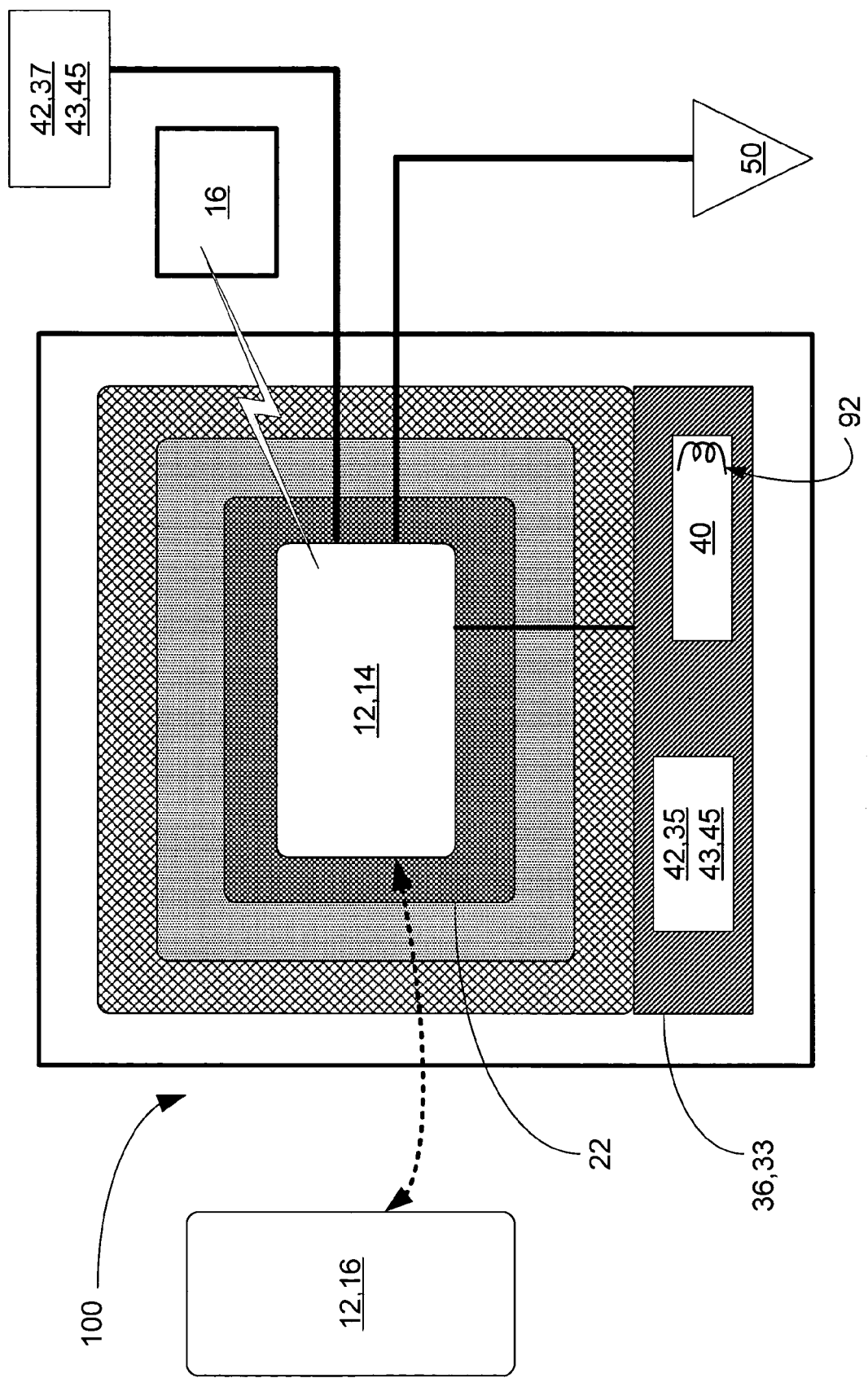
FIG. 3 shows a block diagram of a second embodiment of the medical HDD monitor of the present invention, which uses a single HDD system.

FIG. 3 shows an alternate embodiment 100, in which a single disk drive 12, which is the primary disk drive 14, is included in the inner enclosure 22. The secondary disk drive 16 is then located external to the patient's body, perhaps on a belt, or on the patient's nightstand. The primary and secondary disk drives 14, 16 are in radio frequency communication with each other, and the secondary disk drive 16 may be backed up periodically, perhaps once a day, or on some other schedule. As before, a grounding structure 50 and signal alert 42 are included. The alert 42 mechanism may be used to remind the patient of the back-up scheduled time.

Referring now also to FIG. 2, the medical HDD monitor 11 is equipped with an electronic emergency signal 48 so that when a medical emergency arises, i.e. heart attack, heart fibrillation, high blood sugar, etc., a signal would go out on the GPS frequencies to advance warning pre-selectable doctors or emergency personnel. These personnel are to relay information to an ambulance. As discussed above, the medical HDD monitor 11 is also equipped with a vibrator and/or buzzer/ringer combination signal alert 42 that will alert the user of dangerously low or high levels of transducer activity, as well as alerting the user of dangerously low level conditions of DC power pack supply.

The emergency signal alert 42 can be implemented in several ways, and the following are meant to show possible variations, but the invention is not meant to be limited to them, and it will be obvious to one skilled in the art that many other variations are possible. As will be discussed below, the alert 42 could be a "local" alert 35, which is implanted in the electronics of the medical monitor 10, or could be a "remote" alert 37, located elsewhere in the user's body, or even external to the user's body.

Referring again now to FIG. 1 as well as to FIGS. 2 and 3, one variation includes a subminiature piezo micro-speaker 43 which is implanted in the electronics of the medical HDD monitor 11 or elsewhere in the body, and which issues a tonal frequency based on moderate frequency (0.5 to 3 kHz) beep signals from inside the human body whenever an emergency in the medical monitor system is detected. The emergency signal alert 42 is distinguished by specific number of tonal beeps (short or long), frequency and tonal pitch (amplitude). The user can classify the emergency at hand with the number of beeps and the beep frequency emitted by the piezo micro-speaker 43.

The piezo micro-speaker 43 can also transmit an emergency voice message due to a "text to speech" algorithm 68 built into firmware or software (on the HDD). The text to speech algorithm 68 then can transmit the emergency voice message via the micro-speaker 43 to issue a verbal warning or emergency message (translated into different languages depending on the country of origin) that can be easily heard by the user. The GPS communication network feature of the medical monitor is used to find out which country the patient is in. If it is Spain, for example, the messages that would be received or transmitted are translated into Spanish before they are broadcast in Spanish as well as the home language of the user. This feature is extremely useful outside the USA.

The user can then hear the message clearly and act accordingly. The message then can be repeated increasing in audible intensity so there's no mistake that the user will not be able to hear it at some level of audible intensity. This is most useful when the user is asleep or in a loud environment.

Another variation is that a small vibrational motor 45 is implanted in the medical monitor electronics or elsewhere in the body. This vibrational motor 45 displays a number of vibrational beats based on the emergency being detected. The vibrational motor 45 is audibly silent but the user can easily detect the small vibrations that emanate from the source. The user will notice a very small vibrational buzzing or beating coming from the location of the medical monitor in the human body. Based on the number of vibrational pulses or beats the user can easily distinguish the specific nature of the emergency and act accordingly.

Yet another variation is that the medical HDD monitor 11 can also transmit an emergency signal through the body to a receiving device 47 that can be carried on the user's belt, i.e. a pager or can be located a short distance away, i.e. on a table in the hospital room. The optical display (LCD or LED) of the pager or receiving device 47 would show the specific nature of the emergency of the medical monitor's system. The pager or receiver 47 would also show the user the specific emergency phone number(s) to call for assistance with a medical technician that will problem-solve the situation.

Alternately, the medical HDD monitor 11 can transmit an emergency signal through the airwaves at long distances. This RF signal can be picked up by the user's doctor or medical personnel team who are equipped with special long-distance receivers 49 that can decipher the medical emergency the proper advice or assistance, i.e. call an ambulance.

As another alternative, the medical HDD monitor 11 can also transmit an emergency signal via the GPS electronics 46 to a satellite receiver which would then transmit an emergency call signal to the user's medical personnel team or hospital. This is most helpful when the user is located some distance from the special receiver of the user's medical team, such as when in another state or country.

Typical emergency signals can be transmitted based on the following medical or monitor problems:

1. Low battery voltage of the medical monitor.

2. Battery can't hold a charge or can be recharged externally.

3. Medical monitor's hard drive is experiencing electrical or mechanical problems.

4. "SMART" technology of the hard drive is communicating hard drive problems.

5. Non-volatile or volatile memory of the medical monitor is defective or not storing data correctly.

6. Body transducers high or low states are crossing a specific threshold of detection, i.e. heart monitor shows the heart is beating too fast or too slow.

7. Body transducers are malfunctioning.

8. Human body's internal baclofen intrathecal pump supply is too low and needs to be refilled with new baclofen.

9. Insulin levels are too high or too low in the bloodstream and hypoglycemia or hyperglycemia is starting to occur.

10. Blood pressure is too high or too low.

11. Blood pulse is too high or too low.

12. Pacemaker is showing signs that it needs to be repaired or replaced

13. Transplantable organ(s) is showing signs of being rejected by the body.

14. Blood clot is forming in the lungs or heart.

15. Heart is beating in an irregular fashion.

16. Anaphylactic shock is commencing.

17. Asthmatic blockage and difficulty in breathing is starting.

18. Internal defibrillator is malfunctioning.

19. Internal pacemaker is malfunctioning.

20. Sleep apnea is starting to occur with difficulty in breathing or total failure to breath.

21. Electromechanical problems with artificial heart.

These are just a few examples of the many emergency situations that the medical HDD monitor 11 can detect, decipher and then transmit emergency signal alerts 42 for quick and early assistance from medical personnel.

The alert signals may be turned off by use of the external programming device 4 when the user has been made aware of and dealt with the emergency state.

As referred to above, the medical HDD monitor 11 has a recharging system 31 that includes a battery pack 36, which preferably includes rechargeable batteries 33. The following description and values used are for illustration purposes only and are not to be construed as limitations. The preferred embodiment utilizes two 4 GB Microdrives, where each drive requires 314 ma to write (approximate value for reading also), and 18 ma in idle mode (@3.3 V). Another 10 ma is assumed for the controller. Thus the current required is 46 ma idle, and 342 peak during writing. It is also preferred that the drives 14, 16 can be turned off by the controller 70 (see FIG. 4 below) while not using them. Recharging preferably uses an induction method of charging. An external power coil 91 preferably is used to inductively couple energy to a subcutaneous receiver coil 92, which, in turn, recharges the batteries 33.

The subcutaneous receiver coil 92 is preferably inserted under the skin in the chest region. A comfortable "muff" (not shown) would hold the external power charging coil 91 in proximity to the subcutaneous receiver coil 92 to perform the charging operation. This could be accomplished at night while the subject is asleep.

A suitable battery 33 type is lithium ion. A single battery 33 can hold 190 mah at 3V in a size approximately 20 mm diameter×3.6 mm thick. To allow at least 24 hours between charging intervals, 8 such batteries 33 could be assembled in a battery pack 36 to supply a total of 1520 mah, in a total size of 22 mm diameter×28.8 mm thick. The expected life of the battery system is a minimum of 5 years, recharging once daily.

An external charger 93 provides appropriate AC to the power coil 91, that also may have sensors 94 to detect the presence of the receiver coil 92 located under the subject's skin. A preferred size of the coils 91, 92 suitable to this task is less than 3" diameter, and ⅝" thick. The frequency of AC operation should preferably be contained between 60 hz and 1 kHz. Most preferred, it should be at 60 Hz, which is the frequency of house current.

Battery charge will last over 24 hours, assuming 2.5 hours total reading and writing (314 ma×2.5 h=785 mah), 24 hours of controller operation (10 ma×24 hours=240 mah), 12 hours of disk idle operation (2×18 ma×12 hours=432 mah). Thus, the total daily power consumption budget is expected to be 785+240+432=1457 mah, which is under the 1520 ma the batteries can supply. Obviously, a larger, or smaller, battery pack may be utilized with longer or shorter operation times.

Battery life is rated at a minimum of 5 years, even with deep cycle operation. This is compatible with the HDD 12 expected life of also 5 years. Thus the replacement cycle of the batteries 33 is to coincide with the replacement cycle of the medical HDD monitor 11 as a whole. In addition, a "sleep-mode" module 69 is also preferably programmed into the software of the system. The "sleep-mode" allows the medical HDD monitor 11 to go into a suspended electrical mode to conserve on battery usage. The drive performance is also optimized to minimize battery use and audible noise. Most drives use power to allow the actuator to move as fast as possible to obtain the fastest data rate. However, for the application of providing a data storage device for the human body and its transducers, the drive does not need to have the fastest data rate and the fastest actuator. Since this technique makes audible noise and consumes power, the less than 20 msec actuator seek time is not a critical requirement. By designing the drive specifically for the minimizing audible noise and rationing power (for example, via a 40-80 msec or larger actuator seek time), the current usage can be dramatically reduced, at least by a factor of 25%.

The induction method of charging should not affect pacemakers and other electromechanical devices in the body if the RF power is kept small and isolated only to the area that the battery pack 36 is contained. However, it is possible that the system may not be suitable for individuals who have medical devices which are very sensitive to electromagnetic interference.

As discussed above, the medical HDD monitor 11 is also preferably provided with a vibrator or ringer or other emergency alert mechanism 42 which can alert the user via an vibrator/ringer emergency signal whenever the power levels have decreased to a low condition.

Figure 4:
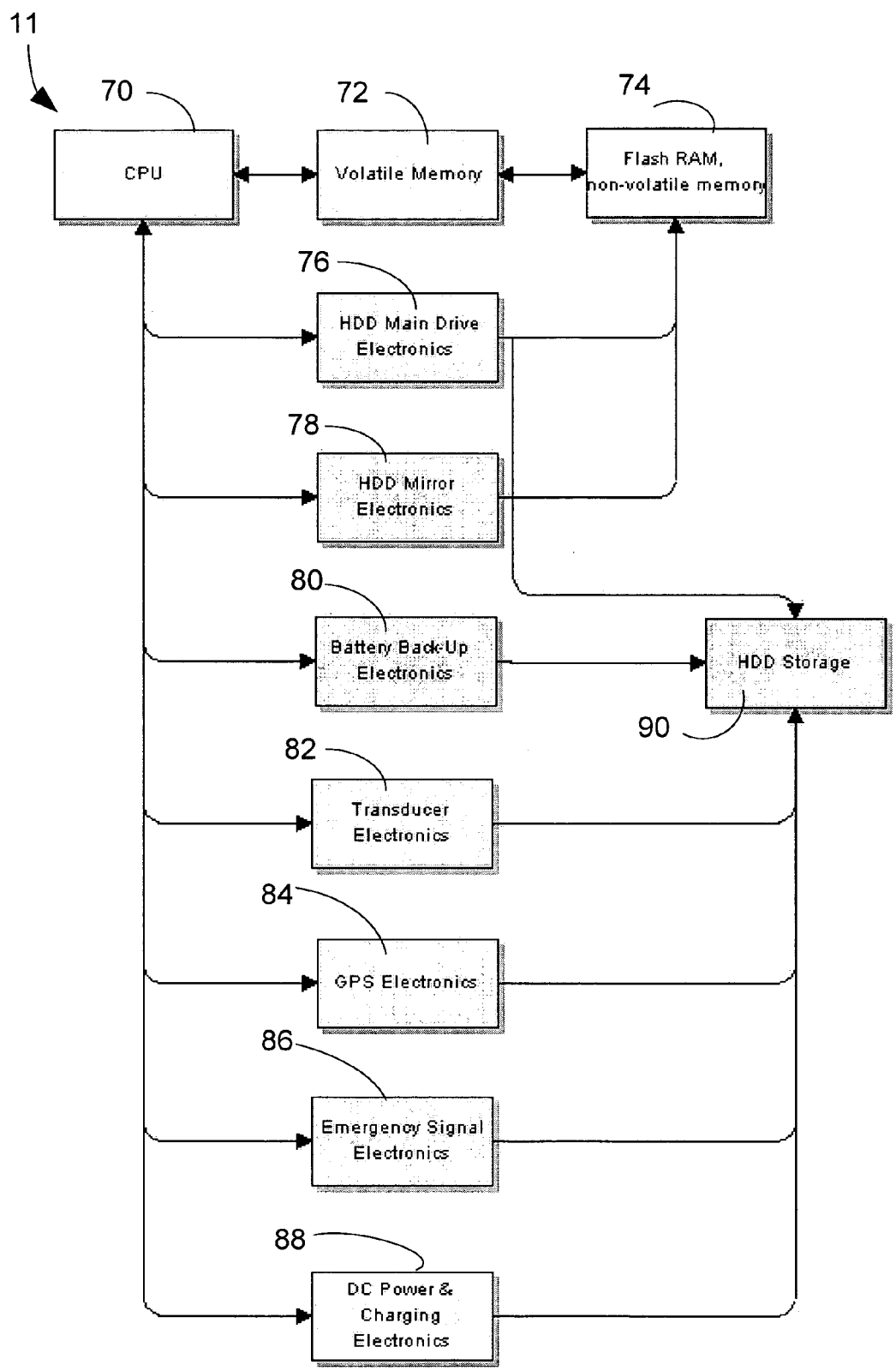
FIG. 4 shows a block diagram of the internal components of the medical HDD monitor of the present invention.

FIG. 4 shows the major component blocks used in the medical HDD monitor 11. A CPU 70 communicates with volatile memory 72, which communicates with Flash RAM, and non-volatile memory 74. The CPU is also in 2-way communication with HDD Main Drive Electronics 76, HDD Mirror Electronics 78, Battery Back-up Electronics 80, Transducer Electronics 82, GPS Electronics 84, Emergency Signal Electronics 86 and DC Power and Charging Electronics, 88, all of which are in communication with the various registers and locations within HDD Storage 90. In addition, HDD Main Drive Electronics 76, HDD Mirror Electronics 78, are in communication with Flash RAM, and non-volatile memory 74.

Figure 5:
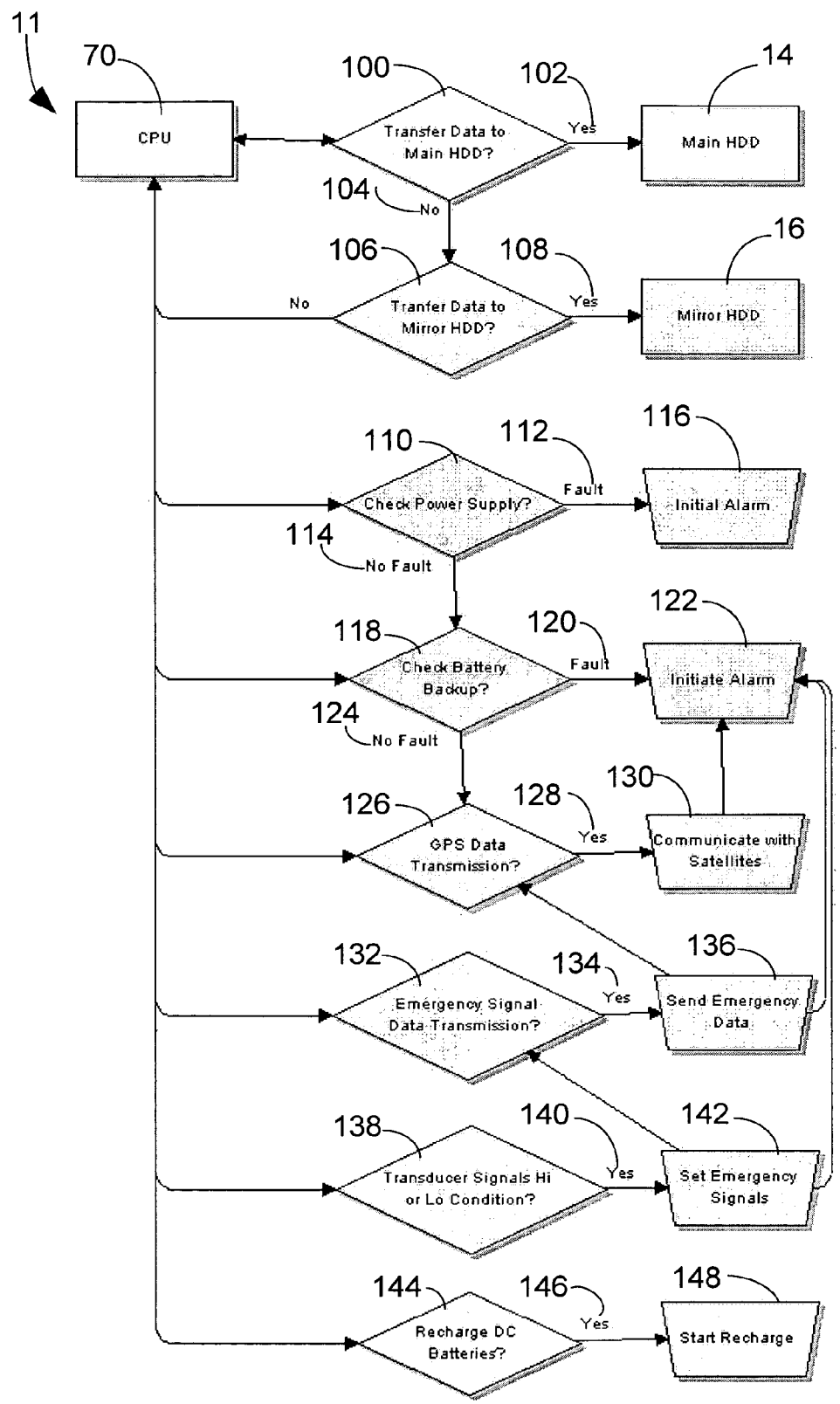
FIG. 5 shows a flow chart showing a software implementation used in the medical HDD monitor of the present invention, which uses a twin HDD system.

FIG. 5 shows a flowchart of major signal routing decisions undertaken by the CPU 70 within the medical HDD monitor 11. A first decision 100 is whether to transfer accumulated data to the primary HDD. If yes 102, then data is sent to the primary HDD 14 (see FIG. 2). If no 104, then a second decision 106 is made whether to transfer data to the secondary, mirror HDD. If yes 108, the data is sent to the secondary HDD 16 (see FIG. 2).

Another decision is made during a check of the power supply 110. If there is a fault 112, an alarm is initiated 116. If there is no fault 114, there is a check of the battery backup 118. If there is a fault 120, an alarm is initiated 122. If there is no fault detected 124, a check is made for GPS data transmission 126. If yes 128 a signal is sent which communicates with satellites 130, which can in turn initiate an alarm 122. This decision 126 can also be initiated by the CPU 70.

A decision to transmit emergency signal data 132 can also be initiated by the CPU 70. If yes 134, emergency data is sent 136, which can include sending data by GPS transmission 126, thus communicating with satellites 130 and initiating an alarm 122.

The CPU also checks if the transducer signals of the sensors 1 (see FIG. 1) are in HI or LOW conditions 138. If yes 140, emergency signals are set 142, transmitted as emergency signal data 132, 136, possibly by GPS transmission 126, 130 to initiate an alarm 122.

The CPU also performs periodic checks to see if the DC batteries need to be recharged 144 according to the current drain rate specification given by the manufacture of the battery pack or batteries. If yes 146, a routine is started to perform the recharge 148.

Figure 6:
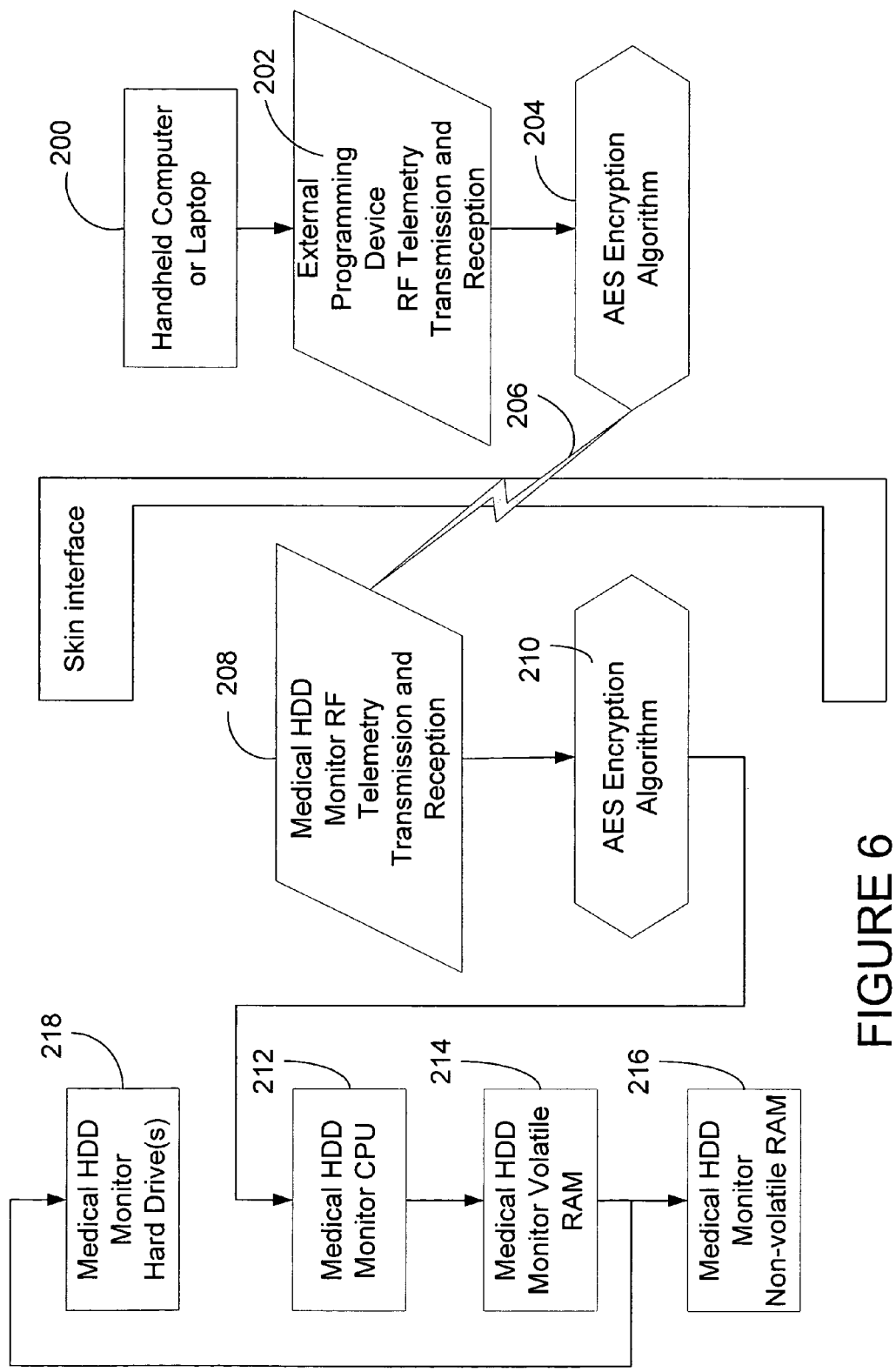
FIG. 6 shows a flow chart showing the setup and programming of the medical HDD monitor by the external programming device.

Referring now to again to FIG. 1 as well as FIG. 6, as mentioned above, the user 1, programmer, doctor, nurse or medical team preferably uses an external programming device 4, to program the initialization and then the final setup of the medical HDD monitor system 10. The external programming device 4 is preferably a small computer, handheld (PDA) 5 or laptop model 6, which allows data transfer to and from the medical HDD monitor 11 via a wire-less transceiver personal network. The communication link is preferably implemented with RF (radio frequency) equipment such as 802.11a, b, or g (or all 3 protocols) or Bluetooth technology. The communication is also preferably hooked with 128-bit data encryption software, AES algorithm or similar, so as to provide a fail-safe and secure data transmission session free of any intrusion from the outside. The 2-way radio frequency link allows the reading of all the transducer sensors 2 in the user's body 1 so the doctor or medical team can readily determine the bio-standard condition of the human body upon initialization of the software and hardware.

The RF communication link uses data encryption and frequency hopping to protect the confidentiality of vital patient information. The communication will allow the medical team to quickly download and upload critical clinical information to and from the medical HDD monitor system 11.

The 802.11 RF communication link employs a chipset that preferably supports both 5 GHz 802.11a and 2.4 GHz 802.11b and 802.11g in its electronics package. The chipset is smaller than the 802.11b-only solutions. The radio frequency (RF) transceiver itself is a single chip supporting both 5 and 2.5 GHz frequencies. The entire 3 chip set (with MAC, baseband, and radio has less than 100 components which keeps the overall physical footprint and financial bill of materials for the chips lower. The chipset also includes support for Wi-Fi Protected Access, AES encryption and the Cisco Compatible Extensions (CXX) which ensures that the client systems will work with Cisco infrastructure equipment. The dual-band RF transceiver package is integrated with both the handheld computer, PDA (or laptop) as well as the Medical Monitor's electronics embedded package.

802.11 is an open standard developed by the Institute of Electrical and Electronic Engineers (IEEE) and currently consists of four different standards: 802.11, 802.11a, 802.11b and 802.11g, 802.11a operates on the license-free 5 GHz frequency band while the others use the 2.4 GHz band. 802.11b is currently the most widespread standard and can transfer data wirelessly at a speed of 5.5 Mbit/s within a range of 50 to 100 meters.

802.11a is four times faster than 802.11b, providing a speed of 27 Mbit/s and a range of 20 to 100 meters. 802.11g is the latest standard and is just as fast as 802.11a but operates on the 2.4 Ghz frequency band.

Bluetooth is a wireless specification delivering short-range radio communication between electronic devices that are equipped with specialized Bluetooth chips. It lets nearly all devices talk to one another by creating a common language between them. All devices such as cell phones, PDAs, pagers, stereos, and other home appliances can communicate and connect using Bluetooth technology to form a private, personal area network (PAN).

The Bluetooth specification standard defines a short range (10-meter) radio link. The devices carrying Bluetooth-enabled chipsets can easily transfer data at a range of 720 kbits/s with 10 meters of range through walls, clothing, luggage bags, and also, through the interface between the skin and muscle tissue and air. The interaction between devices occur by itself without direct human intervention whenever they are within each other's range. In this process, the software technology embedded in the Bluetooth transceiver chip triggers an automatic connection to deliver an "accept the data flow" signal (with data encryption methods to protect the security of information).

Each Bluetooth-enabled device contains a 1.5-inch square transceiver chip prefereably operating in the ISM (industrial, scientific, and medical) radio frequency band of 2.40 GHz to 2.48 Ghz. This frequency is generally available worldwide for free without any licensing restrictions. The ISM band is divided into 79 channels with each carrying a bandwidth of 1 MHz.

In each transceiver chip, software is embedded called the link controller. This mechanism performs the functions of identifying other Bluetooth devices, connecting and transferring of data. Whenever devices carrying Bluetooth technology are within each other's range, they create an automatic ad hoc PAN (personal area network) called a piconet. In this arrangement, one device acts as the "master" such as a laptop or PDA, while other devices function as "slaves" such as printers, scanners, or the Medical Monitor. A piconet normally carries up to 8 devices. The master device decides if a particular communication service is needed from a slave device.

At the time when a connection is made between Bluetooth devices, an exchange of unique Bluetooth identity called global ID takes place. A device global ID indicates its profile along with capability functions. Upon matching of the device profiles, a connection is made and as the devices exchange data (with data encryption), the Bluetooth transceiver chip hops back and forth among frequencies (frequency hopping).

A scatternet forms if a device from a piconet also acts as a member of another piconet. In this scheme, a device being master in one piconet can simultaneously be a slave in the other one.

Due to the aspect of radio waves, the security concerning can be addressed with 3 aspects: specific sequence of channel hopping known only to the sending and receiving devices, challenge-response authentication routine to verify the validity of the receiving unit, and the 128-bit key encryption standard for securing transmission between devices.

One can create a personal area network at home or on the road with Bluetooth-enabled devices such as a keyboard, mouse, scanner, PDA, laptop, cell phone, Medical Monitor, etc. This network can automatically help synchronize notes, calendar, address book and medical information.

The setup and programming is shown in the flow diagram of FIG. 6. The sequence is started when a handheld computer or laptop 200 prepares data for RF telemetry transmission and reception 202. This is encrypted by the AES encryption algorithm 204 and sent through the skin interface 206 of the user, where it is received by the medical HDD monitor's RF telemetry transmission and reception module 208. This is decrypted by the AES encryption algorithm 210, and sent to the medical monitor CPU 212 where it is sent to the medical monitor's volatile RAM 214. From there it may be sent to the medical HDD monitor's non-volatile RAM 216 or to the medical HDD monitor's hard drive or drives 218.

While the present invention has been shown and described with regard to certain preferred embodiments, it is to be understood that modifications in form and detail will no doubt be developed by those skilled in the art upon reviewing this disclosure. It is therefore intended that the following claims cover all such alterations and modifications that nevertheless include the true spirit and scope of the inventive features of the present invention.

What is claimed is:

1. A medical monitor for implantation in the user's body for monitoring data on biological activity and states gathered from sensors implanted in the user's body, said medical monitor comprising:

a primary disk drive and a secondary disk drive, wherein said secondary disk drive mirrors said primary disk drive, said primary drive and a secondary drive being in communication with each other, to provide disk drive data redundancy and data backup, and where said disk drive data redundancy and data backup is accomplished by an operating configuration chosen from the group consisting of RAID 0, RAID 1, and RAID 0+1 techniques;

an alert mechanism which signals the user that a back-up to said secondary hard disk drive is scheduled to be performed;

an enclosure surrounding said primary drive and said secondary drive, where said enclosure is adapted to be implanted within the body of a user; and a transmitter and receiver for producing and transmitting signals, said medical monitor being in communication with said sensors, by which information on biological activity and states is stored on said primary and secondary disk drives.

2. The medical monitor of claim 1, wherein:
said alert mechanism includes a piezo micro-speaker.

3. The medical monitor of claim 1, wherein:
said alert mechanism includes a vibration motor.

4. The medical monitor of claim 1, wherein:
said alert mechanism is a local alert.

5. The medical monitor of claim 1, wherein:
said alert mechanism is a remote alert.

6. A system for monitoring biological activity and states in the body of a user, comprising:

a medical HDD monitor, including a primary disk drive and a secondary disk drive, wherein said secondary disk drive mirrors said primary disk drive, said primary drive and a secondary drive being in communication with each other, to provide disk drive data redundancy and data backup, and where said disk drive data redundancy and data backup is accomplished by an operating configuration chosen from the group consisting of RAID 0, RAID 1, and RAID 0+1 techniques, an alert mechanism which signals the user that a back-up to said secondary hard disk drive is scheduled to be performed, and a transmitter and a receiver for producing and transmitting signals in the radio frequency range;

an enclosure surrounding said primary drive and said secondary drive, where said enclosure is adapted to be implanted within the body of a user;

at least one sensor for communicating data from at least one site in said body of said user to said medical HDD monitor; and an external programming interface which communicates with said medical HDD monitor by radio frequency transmission, in order to set performance parameters of said medical HDD monitor.

7. The system of claim 6, further comprising:
an external programming device which is in radio frequency communication with said medical HDD monitor.

8. The system of claim 7, wherein:
said external programming device is chosen from a group consisting of hand-held computers and laptop computers.

* * * * *